US012593958B2

(12) United States Patent (10) Patent No.: US 12,593,958 B2
Withers et al. (45) Date of Patent: Apr. 7, 2026

(54) ENDOSCOPE

(71) Applicant: TTP PLC., Royston (GB)

(72) Inventors: Michael Withers, Royston (GB); Paul Galluzzo, Royston (GB); Duncan Stuart Mcbryde, Royston (GB); Rita Stella, Royston (GB)

(73) Assignee: TTP Plc., Royston (GB)

( * ) Notice: Subject to any disclaimer, the term of this patent is extended or adjusted under 35 U.S.C. 154(b) by 393 days.

(21) Appl. No.: 18/020,679

(22) PCT Filed: Aug. 11, 2021

(86) PCT No.: PCT/GB2021/052086
§ 371 (c)(1),
(2) Date: Feb. 10, 2023

(87) PCT Pub. No.: WO2022/034323
PCT Pub. Date: Feb. 17, 2022

(65) Prior Publication Data
US 2023/0329523 A1      Oct. 19, 2023

(30) Foreign Application Priority Data

Aug. 12, 2020    (GB) ..................................... 2012570
Aug. 12, 2020    (GB) ..................................... 2012572
Aug. 12, 2020    (GB) ..................................... 2012573
Aug. 13, 2020    (GB) ..................................... 2012626

(51) Int. Cl.
*A61B 1/00*       (2006.01)
*A61B 1/005*      (2006.01)
*A61B 1/018*      (2006.01)
*A61B 1/05*       (2006.01)
*A61B 1/06*       (2006.01)
*G06T 7/246*      (2017.01)

(52) U.S. Cl.
CPC .... *A61B 1/000095* (2022.02); *A61B 1/00082* (2013.01); *A61B 1/00148* (2022.02); *A61B 1/0051* (2013.01); *A61B 1/018* (2013.01); *A61B 1/05* (2013.01); *A61B 1/0676* (2013.01); *G06T 7/248* (2017.01); *G06T 2207/10068* (2013.01)

(58) Field of Classification Search
CPC ............ A61B 1/00082; A61B 1/00148; A61B 1/00009; A61B 1/000094; A61B 1/00006
See application file for complete search history.

(56) References Cited

U.S. PATENT DOCUMENTS

| | | | |
|---|---|---|---|
| 5,916,145 A | 6/1999 | Chu et al. | |
| 2008/0091063 A1 | 4/2008 | Terliue | |
| 2008/0269559 A1* | 10/2008 | Miyamoto | ......... A61B 1/00177 600/116 |
| 2010/0076263 A1 | 3/2010 | Tanaka et al. | |

(Continued)

OTHER PUBLICATIONS

PCT Patent Application No. PCT/GB2021/052086 International Search Report and Written Opinion dated Jan. 17, 2022.

*Primary Examiner* — Alexandra L Newton
(74) *Attorney, Agent, or Firm* — Erise IP, P.A.

(57) ABSTRACT

A computer-implemented method for controlling an endoscope having a flexible tubular body, the method comprising: deploying an anchor to stabilise at least a part of the flexible tubular body; and performing active image stabilisation to stabilise the position of a camera at a distal end of the endoscope.

20 Claims, 17 Drawing Sheets

(56)           References Cited

U.S. PATENT DOCUMENTS

| | | | |
|---|---|---|---|
| 2013/0165753 A1* | 6/2013 | Takahashi | G02B 23/2476 |
| | | | 382/128 |
| 2017/0079511 A1 | 3/2017 | Leanna et al. | |
| 2017/0215701 A1* | 8/2017 | Wake | A61B 1/00148 |
| 2017/0258295 A1* | 9/2017 | Kronman | A61B 1/000094 |
| 2018/0332227 A1* | 11/2018 | Inose | H04N 23/6811 |
| 2019/0380798 A1* | 12/2019 | Itkowitz | A61B 1/3132 |
| 2021/0076907 A1* | 3/2021 | Kurihara | A61B 1/0016 |

* cited by examiner

S-bend causes loop (green)

Loop avoided: balloon with tension (blue)

Frame n

Frame n+1

Frame n+2

Stabilisation disabled

Stabilisation enabled

161 — Obtain a first image and a second image of an internal cavity captured at different times by a camera in a distal end portion of an endoscope 162 — Compare the first and second image to determine an endoscope motion of the distal end portion relative to a feature of the internal cavity 163 — Control an actuator to compensate for the endoscope motion

ENDOSCOPE

RELATED APPLICATIONS

The present application is a national stage application under 35 U.S.C. § 371 of International Application No. PCT/EP2021/052086, filed Aug. 11, 2021, which claims priority to Great Britain Patent Application Nos. 2012570.4, filed Aug. 12, 2020; 2012572.0, filed Aug. 12, 2020; 2012573.8, filed Aug. 12, 2020; and 2012626.4, filed Aug. 13, 2020. The above referenced applications are hereby incorporated by reference in their entirety.

TECHNICAL FIELD

The invention relates to endoscopes for remotely observing or interacting with internal cavities of a patient, such as lumens of the gastrointestinal tract or the lungs or larger cavities such as the abdominal cavity or thoracic cavity.

BACKGROUND

Endoscopes are increasingly used as a less invasive option for many medical procedures such as colonoscopy, bronchoscopy, and laparoscopic and thoracoscopic surgeries.

An endoscope comprises a proximal end and a distal end connected by a tubular body. The distal end is inserted into the patient to reach an internal cavity where medical observation or intervention is required, while the proximal end includes or connects to a control system. Once deployed, a camera, lights and/or other tools at the distal end are used to perform the required observation and/or intervention.

In order to observe or intervene with an area of interest of an internal cavity of a patient, the distal end of the endoscope must be able to maintain a stable, and preferably precise, position. The endoscope is typically long (in some cases, up to 1.6 m long), and its tubular body is in many cases flexible to enable following the shape of an internal lumen. Flexibility and precise manoeuvrability are key requirements for an endoscope so a patient's body may be navigated without causing damage. In navigating curved pathways it is helpful to be able to actively steer the endoscopic tools by inducing curvature, in particular being able to steer the end of the endoscope and allow the rest of the endoscope to be flexible and passively follow the curvature of the lumen. The length and/or flexibility of the endoscope make it difficult to ensure stability of the distal end by controlling the proximal end of the endoscope.

Accordingly, it is desirable to provide ways for improving the stability of the distal end of an endoscope.

SUMMARY

According to a first aspect, the present disclosure provides a computer-implemented method for controlling an endoscope having a flexible tubular body, the method comprising: deploying an anchor to stabilise at least a part of the flexible tubular body; and performing active image stabilisation to stabilise the position of a camera at a distal end of the endoscope.

By combining active image stabilisation with using an anchor, the effort required to stabilise the camera (and other tools at the distal end of the endoscope) is reduced, and stabilisation can be more effectively performed.

Optionally, performing active image stabilisation comprises controlling a bending shape or a bending force in a portion of the flexible tubular body between the anchor and a distal end of the flexible tubular body.

By stabilising only the portion of the endoscope which is beyond the anchor, the computation resources required for stabilisation can be reduced.

Optionally, the anchor is attached to the flexible tubular body via a slider defining a range of movement of the flexible tubular body relative to the anchor, and performing active image stabilisation comprises controlling a position of the flexible tubular body relative to the anchor.

Stabilising by moving the tubular body relative to the anchor provides an additional stabilisation option which can simultaneously increase or decrease the length of the endoscope beyond the anchor and thus increase or decrease the range of freedom of movement for the endoscope using its flexibility.

Optionally, performing active image stabilisation comprises: determining that image stability is below a predetermined lower threshold; and redeploying the anchor to reduce a distance between the anchor and a distal end of the flexible tubular body.

Optionally, performing active image stabilisation comprises: determining that image stability is below a predetermined lower threshold; and deploying an additional anchor between an already-deployed anchor and a distal end of the flexible tubular body.

Optionally, performing active image stabilisation comprises: determining that image stability is below a predetermined lower threshold; and controlling the anchor to increase an anchoring strength.

Optionally, the anchor is an expandable anchor and increasing an anchoring strength comprises increasing a size or stiffness of the anchor.

Actively controlling the anchor deployment as part of image stabilisation provides an additional route for improving stability using a mixture of large changes to the degree of freedom using the anchor and fine tuning using the flexibility of the tubular body.

Optionally, performing active image stabilisation comprises: determining that image stability is above a predetermined upper threshold; and redeploying the anchor to increase a distance between the anchor and the distal end of the flexible tubular body.

Optionally, performing active image stabilisation comprises: determining that image stability is above a predetermined upper threshold; and removing the deployed anchor.

Optionally, performing active image stabilisation comprises: determining that image stability is above a predetermined upper threshold; and controlling the anchor to reduce an anchoring strength.

Optionally, the anchor is an expandable anchor and reducing an anchoring strength comprises reducing a size or stiffness of the anchor.

Actively controlling the anchor deployment can further reduce the risk of over-stabilisation, and ensure that the operator has optimised freedom to move the endoscope during observation or intervention.

According to a second aspect, the present disclosure provides an endoscope for remotely observing or interacting with an internal cavity of a patient, the endoscope comprising a distal end portion that reaches the internal cavity in use, wherein the distal end portion comprises a main body and a stabilising anchor suitable for expanding when the distal end portion is positioned at the internal cavity.

By using an expanding anchor, a size of the distal end portion can be relatively small for manoeuvring the endoscope into position and then, after the stabilising anchor is expanded, the stability of the position of the distal end portion can be improved.

Optionally, the stabilising anchor is configured to expand between the main body of the distal end portion and a wall of the cavity.

By arranging the stabilising anchor in its expanded state between the main body and the wall of the cavity, the stabilising anchor can fix a relative position between the main body and wall, and thus stabilise a position of endoscope tools such as a camera or surgical tool relative to a feature of the wall.

Optionally, the distal end portion comprises a plurality of stabilising anchors arranged circumferentially around the main body of the distal end portion.

By using a plurality of anchors, the distal end portion of the endoscope can be stabilised relative to multiple reference points on the wall of the cavity, meaning that the position of the distal end portion can be stabilised without the main body of the distal end portion of the endoscope being in contact with the wall of the cavity.

Optionally, a first stabilising anchor of the plurality of stabilising anchors is configured to expand to a greater width than a second stabilising anchor of the plurality of stabilising anchors.

By using a plurality of anchors which expand to different widths, the distal end portion of the endoscope can be stabilised at an off-centre position within the internal cavity of the patient. The off-centre position can be configured to a position which is preferred for performing a particular required observation or interaction in a given medical context.

Optionally, the stabilising anchor comprises a sleeve surrounding the main body of the distal end portion.

By using a sleeve surrounding the main body as a stabilising anchor, the position of the stabilising anchor relative to the main body can be more predictably controlled, and deployment of the expanded stabilising anchor is simplified.

Optionally, the stabilising anchor is configured to expand by inflation.

By providing a stabilising anchor which expands by inflation, expansion or reduction of the stabilising anchor can be controlled by adding or removing fluid from the stabilising anchor.

Optionally, the stabilising anchor is configured to be filled with a predetermined quantity of fluid.

By filling the stabilising anchor with a predetermined quantity of fluid, a size of the anchor after expansion can be controlled according to the size of the cavity in which the anchor is to provide stabilisation.

Optionally, the stabilising anchor is configured to be filled to a predetermined gas pressure.

By filling the stabilising anchor to a predetermined gas pressure, both a size and a stiffness of the expanded anchor can be controlled. The stiffer the anchor is, the more stretching force that the anchor applies to soft tissues of the internal cavity of the patient, and by controlling the gas pressure, the stretching force can be limited so that anchoring is provided while reducing the risk of damage to the internal cavity of the patient.

Optionally, the distal end portion comprises a gas canister.

By providing a gas canister in the distal end portion of the endoscope, the distal end portion can be self-contained in terms of the anchoring function provided by the stabilising anchor.

Optionally, the endoscope further comprises a proximal end portion configured to remain outside the patient and a fluid connection between the proximal end portion and the stabilising anchor of the distal end portion.

By providing a fluid connection between the proximal end portion and the stabilising anchor, expansion (and optionally reduction) of the stabilising anchor can be controlled along with other endoscope functions controlled at or through the proximal end portion, and a quantity of fluid filling the stabilising anchor can be adapted for different medical contexts.

Optionally, the stabilising anchor comprises a resilient portion.

A resilient portion can be configured to stabilise the distal end portion without requiring a fluid supply for expanding the stabilising anchor.

Optionally, the stabilising anchor comprises a first base portion, a second base portion, and the resilient portion between the first anchor portion and the second anchor portion, wherein the stabilising anchor is configured to expand by decreasing a distance between the first attachment portion and the second attachment portion. This configuration enables mechanical control of a quantity of expansion of the resilient element.

Optionally, the stabilising anchor is attached to the main body of the distal end portion. By attaching the stabilising anchor to the main body, the stabilising anchor can be manoeuvred into position along with the rest of the distal end portion, and can be immediately expanded when the distal end portion is in a required position.

Optionally, the stabilising anchor is attached to the main body of the distal end portion via a slider defining a range of movement of the stabilising anchor relative to the main body.

By providing a sliding attachment between the main body and the stabilising anchor, a position of the distal end portion can be stabilised while still allowing for some constrained motion of the main body which is used for observing or interacting with features of interest in the internal cavity of the patient. For example, this can provide a stable datum position of the distal end portion relative to a feature of interest, while still allowing deliberate motion of the main body relative to the stable datum position.

Optionally, the slider is configured to move axially along the main body.

By configuring the slider to move axially, the distal end portion can be stabilised with an anchor near to a location of interest in the internal cavity, and the main body can be moved beyond the stabilising anchor to reach the location of interest with a larger range of motion due to an increased length of the endoscope extending between the stabilising anchor and the location of interest.

Optionally, the endoscope further comprises a line connected between the proximal end portion and the slider for controlling or locking a position of the slider.

By adjusting the length or tension of the line, a position of the slider can be fixed or moved, to adjust a position of the stabilising anchor relative to the proximal end of the endoscope.

Optionally, the stabilising anchor is configured to be stored in a working channel of the endoscope and to be deployed from the working channel before expansion.

Endoscopes frequently have one or more working channel that runs internally along the tubular body of the endoscope. These are used for deploying tools such as cameras, lights or surgical instruments at the distal end of the endoscope.

By storing the stabilising anchor in a working channel, a size of the distal end portion can be reduced while it is being manoeuvred into position in the internal cavity of the patient. Once the distal end portion is at or near a required position, the stabilising anchor can be deployed from a distal end of the working channel, attached to the main body of the distal end portion, and expanded to perform its stabilising anchor function. The stabilising anchor may be configured to attach to a slider after it is deployed from the working channel.

According to a third aspect, the present disclosure provides an endoscope comprising: an outer sheath for insertion into a patient; an inner scope movably positioned within the outer sheath; an anchor positioned on the distal end of one of the outer sheath and the inner scope; and a cable fixed to the proximal end of the outer sheath and threaded through a connector on the distal end of the inner scope such that, in use, the cable can be pulled by an operator to distal ends of the outer sheath and inner scope towards one another when the anchor has been activated.

The anchor may be an inflatable balloon or some other form or remotely actuatable anchoring mechanism which can engage with the wall of a passageway to retain the distal end to which it is attached in a fixed position while it is activated.

Optionally, both the outer sheath and inner scope have anchors at their distal ends.

By providing an endoscope with a structure which allows the advancing of one element of an endoscope and then anchoring that to the lumen so that a second element can be advanced by pulling using the tension member attached to the anchored element, eliminates the need to push the second element of the endoscope. This has the advantage of not buckling the passageway through which the endoscope is being passed, improving the ease of navigation of the endoscope by a user. It also reduces the possibility of buckling in the endoscope and reduces the potential of damage being caused to a patient.

According to a fourth aspect, the present disclosure provides an endoscope system for remotely observing a target area of an internal cavity of a patient, the endoscope system comprising an endoscope having a distal end portion that reaches the internal cavity in use, the distal end portion comprising a camera configured to obtain an image of the internal cavity and an actuator configured to control a position of the distal end portion, the endoscope system further comprising a processor configured to: compare a first and second image of the internal cavity obtained at different times by the camera in order to determine an endoscope motion of the distal end portion relative to a target area of the internal cavity; and control the actuator to compensate for the endoscope motion.

By controlling an actuator of the distal end portion based on images obtained by a camera of the distal end portion, motion of the endoscope can be compensated, and stabilisation of the distal end portion is improved. This assists an operator in observing features of interest within the internal cavity of the patient and, in cases where the endoscope also carries tools for medical intervention, assists the operator in interacting with the features of interest.

Optionally, comparing the first and second image comprises: for each of the first and second images, identifying a feature of the target area and a position of the feature; determining a motion of the feature; and determining the endoscope motion based on the motion of the feature.

By tracking the motion of a specific feature, the distal end portion can be maintained at a stable displacement relative to the feature.

Optionally, comparing the first and second image comprises: for each of the first and second images, identifying a plurality of features of the target area and a position of each of the plurality of features; determining a motion of each of the plurality of features; determining the endoscope motion based on an average of the motions of the plurality of features.

By tracking the motion of multiple features, the distal end portion can be maintained at a more accurate stable displacement relative to the plurality of features.

Optionally, comparing the first and second image comprises calculating optical flow between the first image and the second image.

By calculating optical flow, stabilisation can be improved without needing to identify and track specific features, and the technique can be generalised for any medical endoscopy context.

Optionally, the optical flow between the first image and the second image is calculated using a Lucas-Kanade algorithm.

The Lucas-Kanade algorithm is effective at tracking irregular solid surfaces because it assumes regional uniformity of motion, and is therefore effective in tracking motion in a medical context.

Optionally, controlling the actuator to compensate for the endoscope motion comprises applying force feedback to maintain a position of the distal end portion.

Endoscopes are used in resilient contexts, often involving muscular tissue, and are thus not only subject to individual jolts but continuously applied forces. Application of force feedback reduces the need for continuous displacement correction.

According to a fifth aspect, the present disclosure provides a method for controlling an endoscope for remotely observing a target area of an internal cavity of a patient, the endoscope having a distal end portion that reaches the internal cavity in use, the distal end portion comprising a camera configured to obtain an image of the internal cavity and an actuator configured to control a position of the distal end portion, the method comprising: comparing a first and second image of the internal cavity obtained at different times by the camera in order to determine an endoscope motion of the distal end portion relative to a target area of the internal cavity; and controlling the actuator to compensate for the endoscope motion.

DETAILED DESCRIPTION

Anchoring Concepts

Herein, an axial direction means a direction along the tubular body of an endoscope between the distal end and proximal end. Where the endoscope is deployed in an internal cavity comprising a lumen such as the gastrointestinal tract, the axial direction is also a direction along the length of the lumen.

On the other hand, a circumferential direction means a direction around the tubular body of the endoscope.

Figure 1:
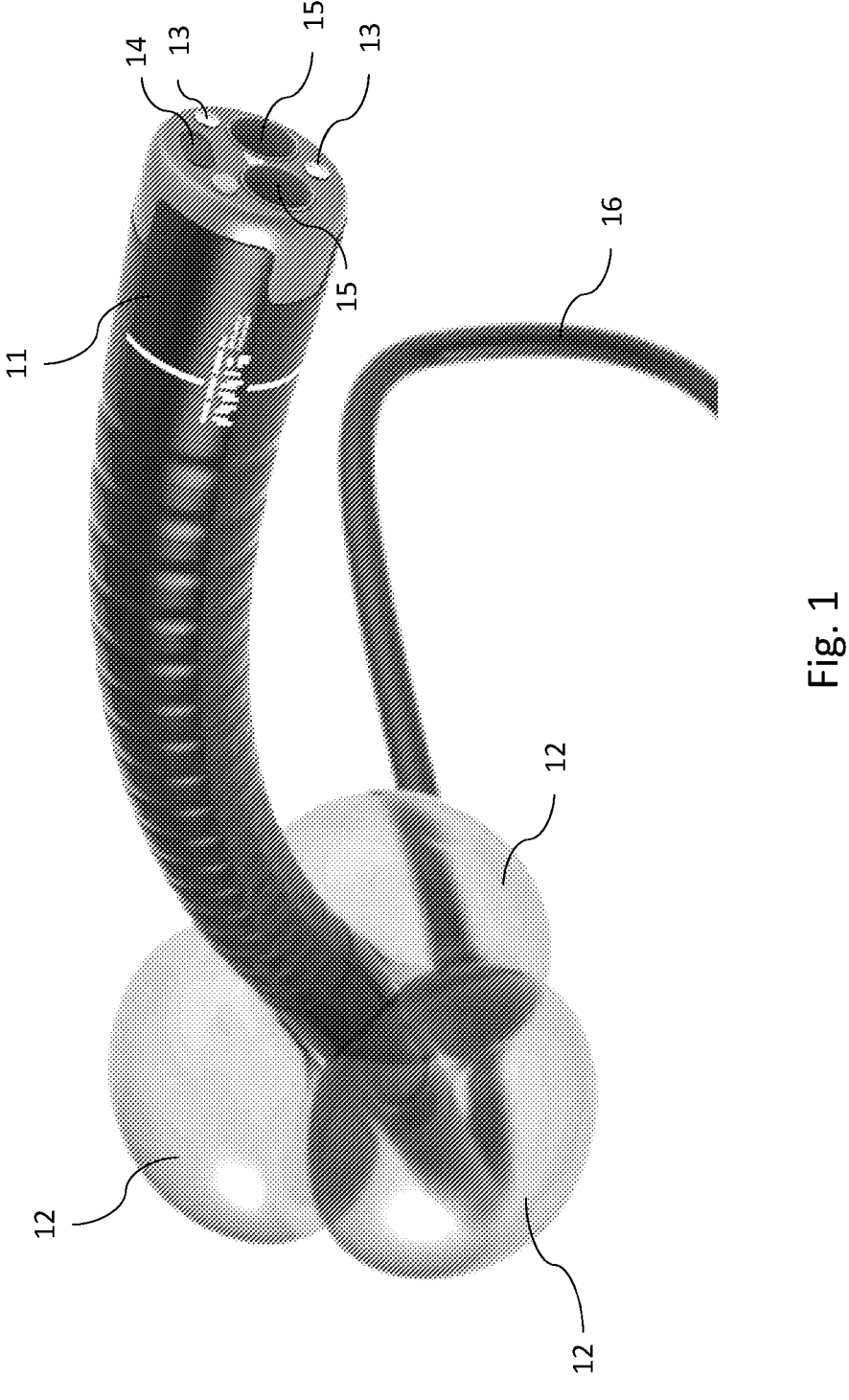
FIG. 1 schematically illustrates a distal end portion of an endoscope used in the invention.

FIG. 1 schematically illustrates a distal end portion of an endoscope according to the invention.

The distal end portion comprises a main body 11 and a plurality of stabilising anchors 12.

The main body 11 is an extension of the tubular body 16 which extends towards a proximal end of the endoscope (not shown).

The tubular body 16 may be flexible. For example, the tubular body 16 may comprise a chain of vertebra which can undergo relative motion to bend the tubular body 16. In this case, bending of the tubular body 16 can be controlled using lines (e.g. wires or chains) connected between individual vertebra of the tubular body 16 and the proximal end of the endoscope (not shown). By adjusting a length or tension of the lines, relative positions of pairs of vertebra can be adjusted such that localised bending of the tubular body 16 occurs. Additionally, any other known mechanism for controlling bending of the endoscope body may be used, such as electronically controlled actuators located along the length of the tubular body 16. This controlled bending may be used to position the distal end portion 11 for observing or interacting with a patient's internal cavity.

Each stabilising anchor 12 may, for example, be an elastic balloon that expands by inflation, such as a Foley catheter balloon. The stabilising anchor 12 may, when expanded, be filled with a predetermined quantity of fluid (e.g. a gas such as air or a liquid such as water), or may be filled to a predetermined gas pressure. Additionally or alternatively, the stabilising anchor 12 may comprise a resilient portion, as described below with reference to FIG. 5.

The stabilising anchor 12 may be filled from a local fluid supply that is integrated with the main body 11 or the stabilising anchor 12, such as a compressed gas canister. Alternatively, the stabilising anchor 12 may be filled using a fluid connection between the proximal end portion (not shown) and the stabilising anchor 12. The fluid connection may for example extend internally along the endoscope between the proximal and distal ends, and may be arranged in a working channel 15. The fluid connection may be opened and closed using a valve at the distal end portion or at the proximal end portion.

When a stabilising anchor 12 is no longer required at a given position, the stabilising anchor may be restored to a stored configuration by releasing the fluid from the stabilising anchor 12.

In FIG. 1, the main body 11 extends in the distal direction past the anchors 12 such that a part of the main body 11 has freedom to move relative to the anchors 12, while the stabilising anchors 12 provide a predictable reference point for controlling this relative motion.

The distal end of the main body 11 comprises one or more lights 13, one or more cameras 14 and distal ends of one or more working channels 15.

The light(s) 13 and camera(s) 14 are used together to see the patient's internal cavity from the distal end of the endoscope. Rather than including electronics at the distal end of the main body 11, the light(s) 13 and camera(s) 14 may comprise optical fibres extending from end to end of the endoscope such that the electronic light source and camera can be located at the proximal end of the endoscope but used to illuminate and see the patient from the distal end of the endoscope. The stabilising anchors 12 stabilise the light(s) 13 and cameras (14) so that observation can be more easily performed.

The working channel(s) 15 are used to hold additional tools such as surgical tools for laparoscopic or thoracoscopic surgeries. The working channel(s) 15 may extend to the proximal end of the endoscope such that tools can be added or removed at the distal end of the endoscope without withdrawing the endoscope from a patient. The stabilising anchors 12 also stabilise such additional tools so that intervention in a patient's internal cavity can be more easily and precisely performed.

Additionally, a working channel 15 may be used to store a stabilising anchor 12 in a stored configuration. When the distal end portion of the endoscope reaches a position where the stabilising anchor is to be deployed, the stabilising anchor 12 can be deployed from the distal end of the working channel 15, expanded, and attached to the outer circumference of the distal end portion.

Figures 2A, 2B:
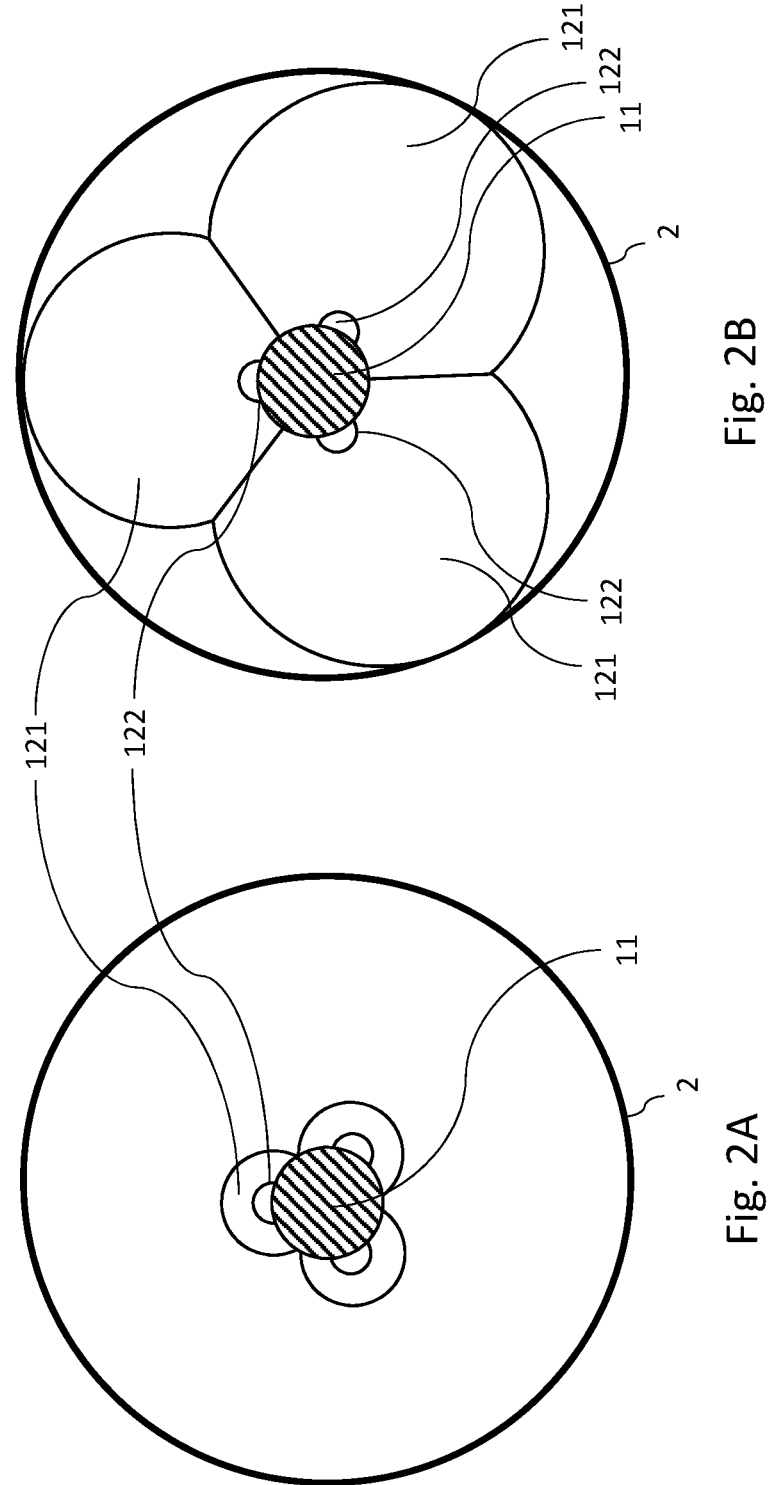
FIGS. 2A and 2B schematically illustrate a plurality of stabilising anchors, respectively in a stored configuration and an expanded configuration.

FIGS. 2A and 2B schematically illustrate a plurality of stabilising anchors, respectively in a stored configuration and an expanded configuration.

More specifically, FIGS. 2A and 2B are schematic cross-sections of an internal cavity 2 of a patient. Inside the internal cavity 2, the main body 11 of a distal end portion of an endoscope according to the invention extends axially lengthwise through the plane of the cross-section.

Referring to FIG. 2A, three stabilising anchors 121 are attached to the main body 11, and are arranged circumferentially around the main body 11. In other embodiments, any number of one or more stabilising anchors 121 may be used.

The attachment between each stabilising anchor 121 and the main body 11 may be a fixed point. However, in FIG. 2A, each stabilising anchor 121 is attached to the main body 11 via a slider 122. Embodiments of the slider 122 are described in more detail below with reference to FIG. 6.

In the stored configuration shown in FIG. 2A, a total cross-section width of the distal end portion of the endoscope is smaller than the cavity 2 (e.g. an internal lumen). This means that the endoscope has space to move along its axial length with relatively little friction.

On the other hand, in the expanded configuration shown in FIG. 2B, each stabilising anchor 12 is expanded between the main body 11 and a wall of the cavity 2. In the expanded configuration, the stabilising anchor 12 supports the endoscope relative to the wall, and the combined effect of a plurality of stabilising anchors arranged circumferentially around the main body 11 is that the stabilising anchors 12 provide a fixed support for the endoscope that resists axial motion due to friction between the stabilising anchors 12 and the wall of the cavity 2.

Figure 3:
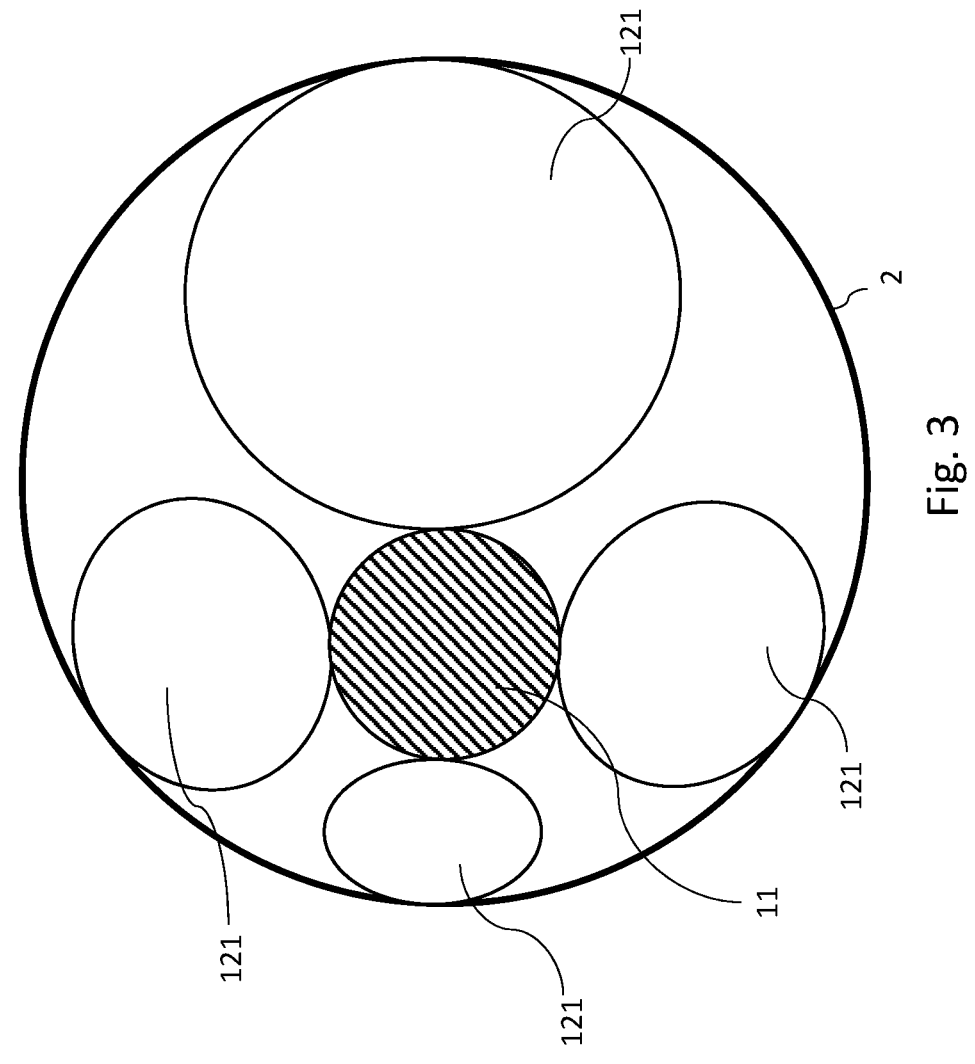
FIG. 3 schematically illustrates a plurality of stabilising anchors configured to expand to different widths.

FIG. 3 schematically illustrates a plurality of stabilising anchors configured to expand to different widths.

More specifically, as with FIGS. 2A and 2B, FIG. 3 shows a schematic cross-section of an internal cavity 2 of a patient. Inside the internal cavity 2, the main body 11 of a distal end portion of an endoscope according to the invention extends axially lengthwise through the plane of the cross-section.

As shown in FIG. 3, by expanding different stabilising anchors to different widths, the main body 11 can be supported in a stable position that is off-centre within the internal cavity 2. This can be used to support the distal end portion close to a target feature of the patient's internal cavity 2.

The different expansion of different stabilising anchors 121 can be controlled by constructing the stabilising anchors from different materials or by constructing the stabilising anchors with different sizes, such as balloons with thicker and more stretchy surfaces or balloons made from different elastic materials. Preferably, however, the different expansion of different stabilising anchors 121 is controlled by expanding each stabilising anchor 121 individually and to a different degree. For example, where the stabilising anchors 121 are inflatable, each stabilising anchor 121 may be filled with a different quantity of fluid. In order to enable different inflation of different stabilising anchors 121, each stabilising anchor 121 may have a separate inflation control, such as a separate fluid connection or a separate valve.

Figures 4A, 4B:
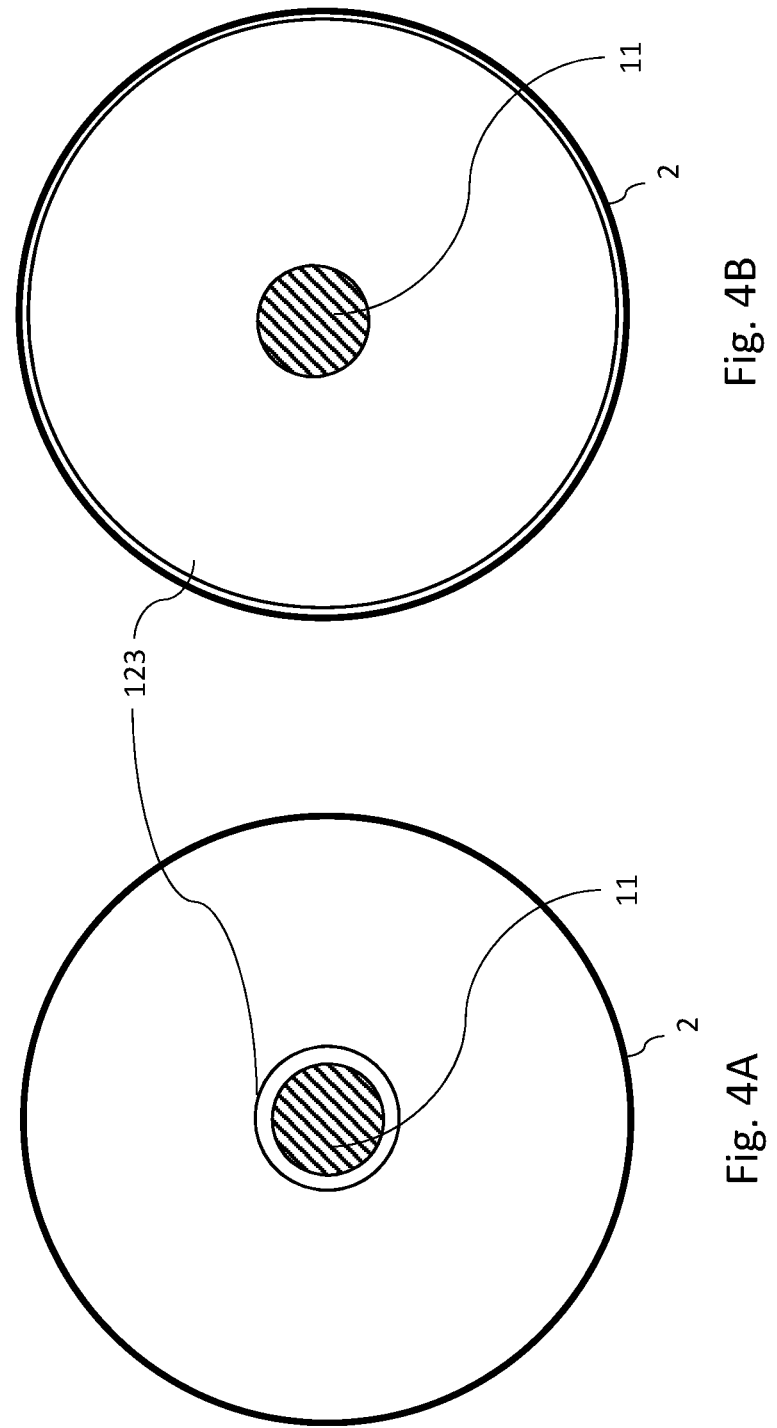
FIGS. 4A and 4B schematically illustrates a stabilising anchor comprising a sleeve, respectively in a stored configuration and an expanded configuration.

FIGS. 4A and 4B schematically illustrates a stabilising anchor 123 in an alternative embodiment, respectively in a stored configuration and an expanded configuration.

More specifically, FIGS. 4A and 4B shows a schematic cross-section of an internal cavity 2 of a patient. Inside the internal cavity 2, the main body 11 of a distal end portion of an endoscope according to the invention extends axially lengthwise through the plane of the cross-section.

The stabilising anchor 123 of FIGS. 4A and 4B comprises a sleeve 123 surrounding the main body 11, as opposed to the balloons shown in FIGS. 1 to 3. This means that the stabilising anchor 123 expands (as shown in FIG. 4B) in all radial directions between the main body 11 and a wall of the internal cavity 2 of the patient. This has the advantage that the sleeve 123 does not need to be oriented in a particular way before expansion.

Figure 5:
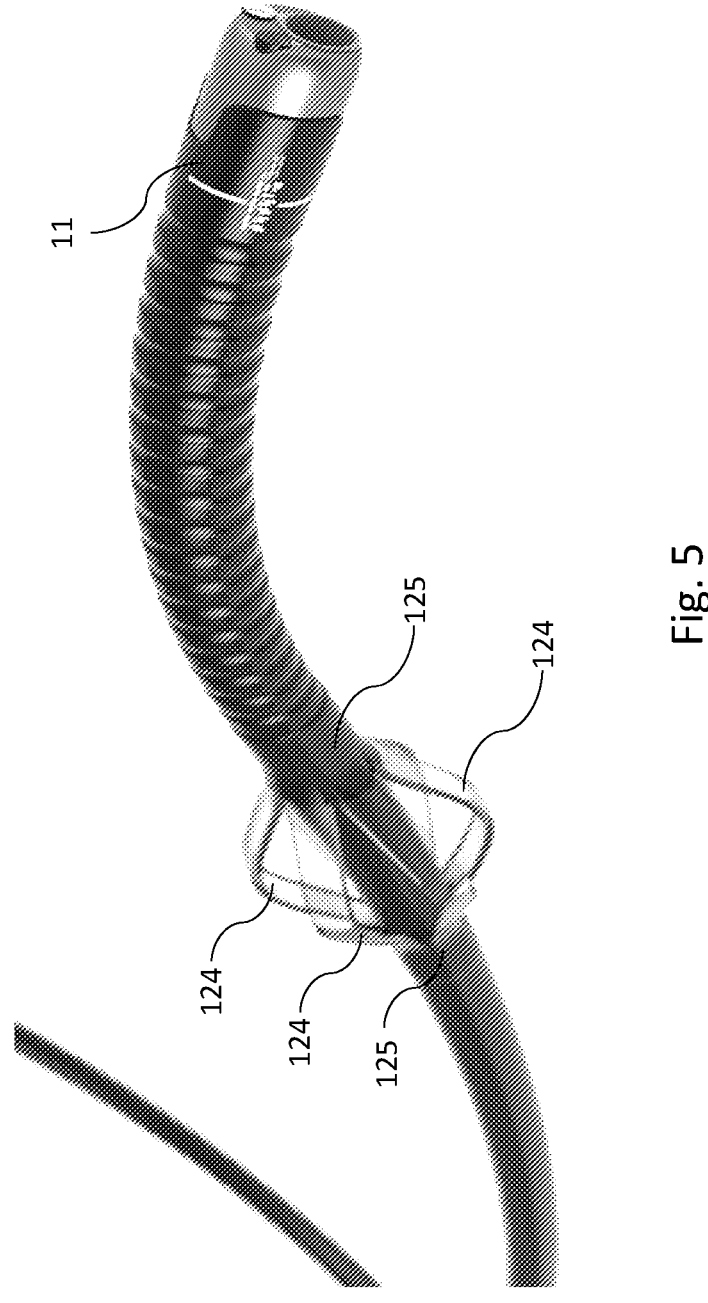
FIG. 5 schematically illustrates a plurality of stabilising anchors comprising a resilient portion.

FIG. 5 schematically illustrates another endoscope comprising a plurality of stabilising anchors 124. This is an alternative embodiment to the above described inflatable stabilising anchors and, in the alternative embodiment of FIG. 5, the stabilising anchors comprise a resilient portion 124 that can bend outwards based on a restoring force for its shape, without the stabilising anchor needing to be filled with a fluid. This embodiment has the advantage that no fluid supply is required.

More specifically, the expanding of the stabilising anchors 124 may be controlled similarly to bending of the tubular body 16 and the main body 11. Expanding of the stabilising anchors 124 can be controlled using lines (e.g. wires or chains) connected to first and second base portions 125, where the resilient portion 124 is between the first and second base portions 125. By decreasing a distance between the first and second base portions 125, the resilient portion 124 is forced to bend outwards. On the other hand, by increasing a distance between the first and second base portions 125, the resilient portion 124 can be flattened into a stored configuration. Additionally, electronically controlled actuators may be used to control the distance between the first and second base portions 125.

A resilient portion 124 as described with reference to FIG. 5 may be combined with an inflatable stabilising anchor as described with reference to FIGS. 1 to 4B, to provide a stabilising anchor that expands both under its own resiliency and based on being filled with a fluid.

Figure 6:
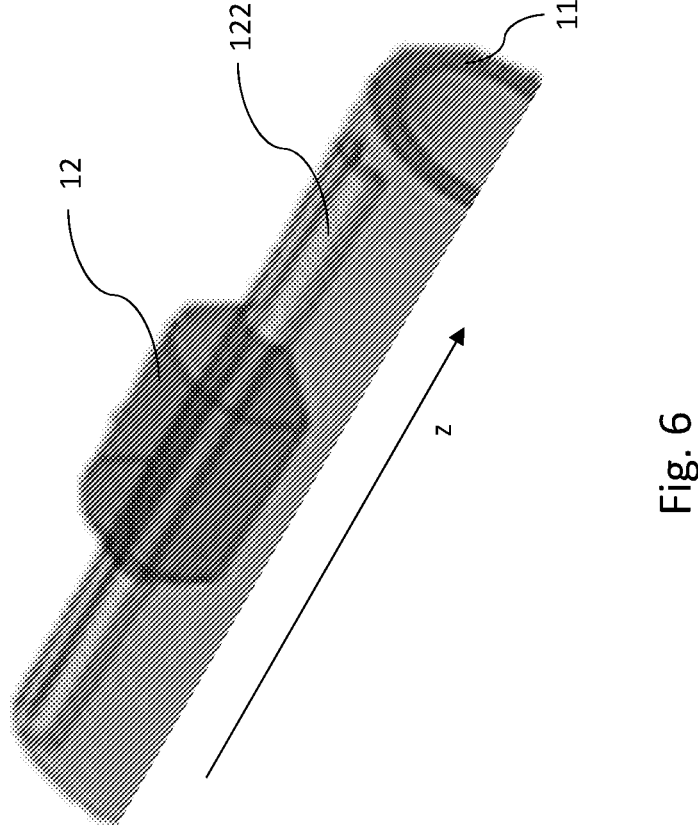
FIG. 6 schematically illustrates a stabilising anchor attached via a slider.

FIG. 6 schematically illustrates a stabilising anchor attached via a slider 122.

The main body 11 and stabilising anchor 12 may each comprise a rail or groove that interlocks with the rail or groove of the other of the main body 11 and stabilising anchor 12. The interlocking rails/grooves allow a predetermined range of motion for the stabilising anchor 12 relative to the main body 11. Any other type of slider may be used to define the range of motion.

The range of motion of the slider is preferably axial motion along a length of the endoscope (the z direction illustrated in FIG. 6). This means that the endoscope can move axially relative to a stabilising anchor that is fixed stably against a wall of the internal cavity 2 of the patient.

The motion of the slider 122 may be controlled similarly to bending of the tubular body 16 and the main body 11, controlled using a line (e.g. wire or chain) connected to the slider 122. Additionally, electronically controlled actuators may be used to control the motion of the slider 122.

In the above described embodiments, usage of one or more stabilisation anchors has been described in the context of a "distal end portion". In general, the above described stabilisation anchors can be used to stabilise any part of the length of an endoscope which is deployed within a patient. Accordingly, "distal end portion" means any part of the tubular body of an endoscope that is configured to be deployed within a patient.

For example, while an endoscope is being snaked along a lumen such as a gastrointestinal tract, and before reaching a target part of the gastrointestinal tract, a stabilisation anchor may be expanded at a current position in the lumen to stabilise the endoscope as it moves past the stabilisation anchor and is snaked further along the lumen. As will be described below, the stabilisation anchor may, for example, be used to reduce rubbing of the endoscope against a wall of the lumen when the endoscope extends around a bend in the lumen.

Furthermore, multiple stabilisation anchors may be used at multiple points along the axial length of an endoscope. The multiple stabilisation anchors may be deployed from a working channel 15, each before the endoscope reaches a respective bend in a lumen along which the endoscope is deployed. A final stabilisation anchor may then be expanded as the distal end of the endoscope approaches a target area of the internal cavity that is to be observed or interacted with.

Advancing an Endoscope Using Anchoring Mechanisms

Figures 7A, 7B:
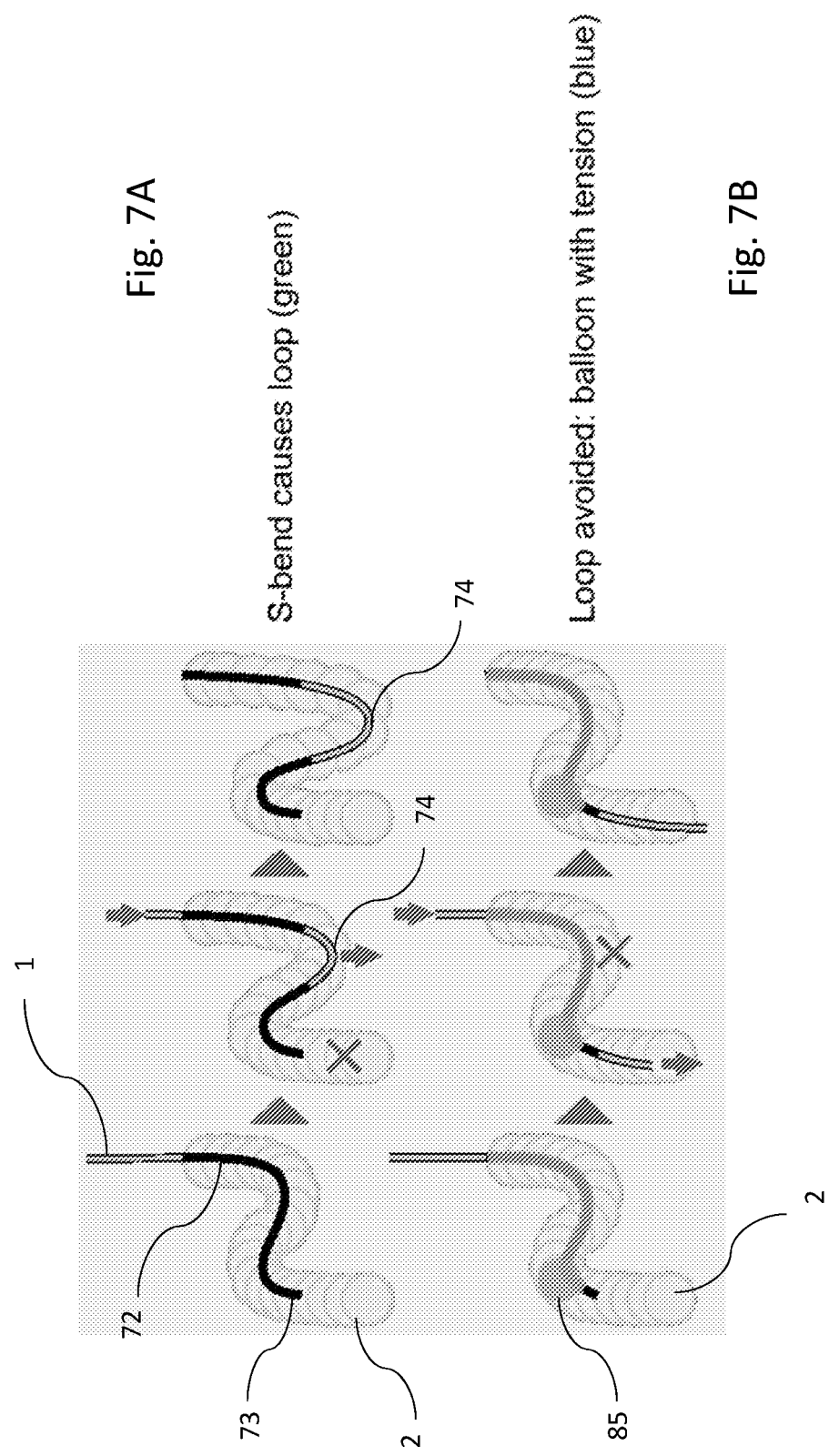
FIG. 7A schematically illustrates an example prior art endoscope during deployment.
FIG. 7B schematically illustrates an example endoscope according to the invention during deployment.

An example prior art endoscope 71 is generally illustrated during deployment in FIG. 7A. The endoscope 71 comprises a body 72 which is inserted into a patient cavity 2, with the distal end 73 being steered during insertion by an operator. As can be seen, if the cavity 2 has a tight radius turn 74 in it the body 72 has to be bent significantly. This can cause large forces to be applied to the cavity as the body 72 is inserted further and can even prevent further movement of the distal end 73, as also shown, as all the force that needs to be applied has to be delivered at the proximal end of the endoscope to drive it forward.

As shown in FIG. 7B, and as will be explained below, the present invention provides an endoscope 1 with anchoring inflatable balloon 85 which overcomes this problem.

Figure 8:
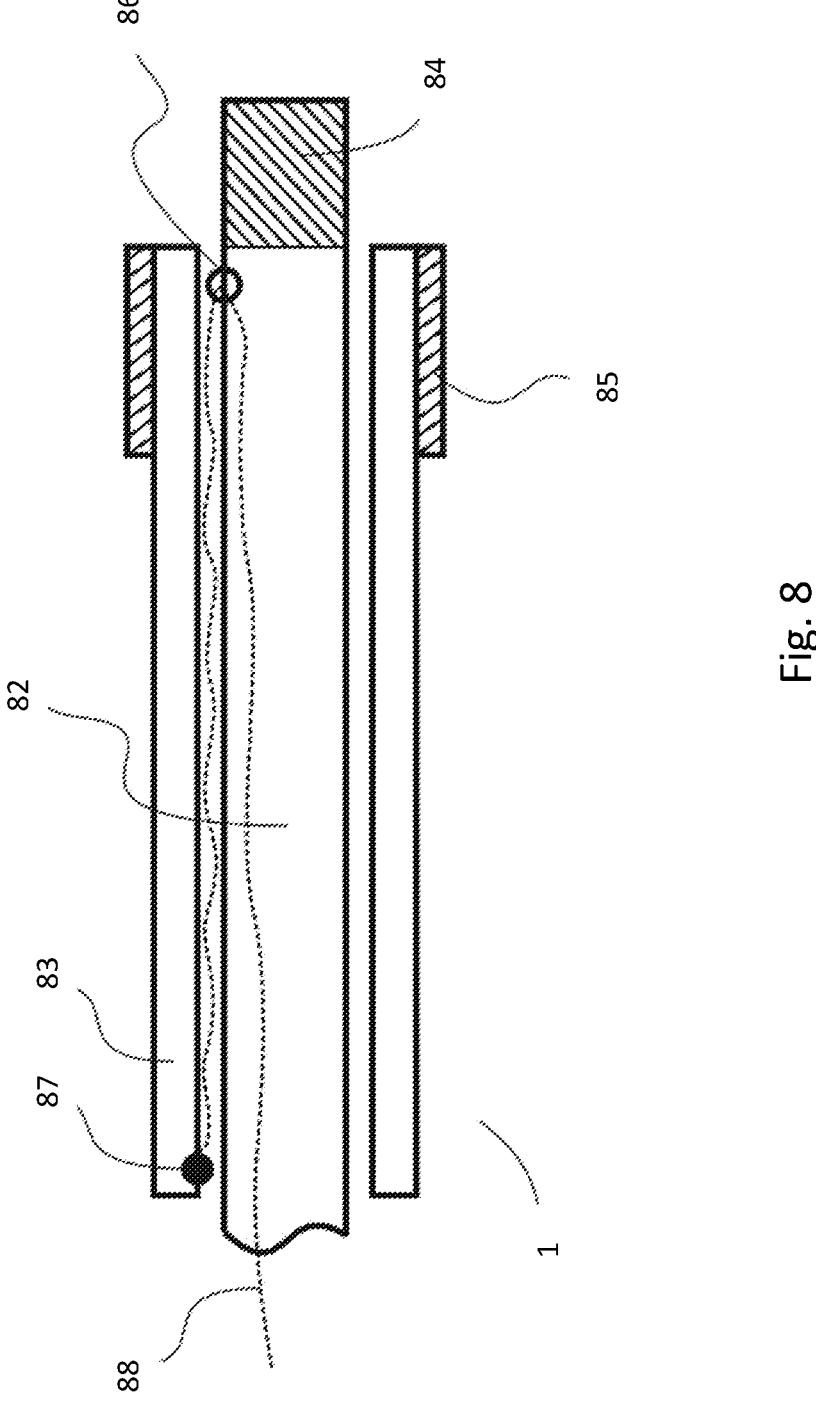
FIG. 8 shows a schematic view of the distal end of an endoscope according to the invention.
Figures 9A, 9B, 9C, 9D, 9E:
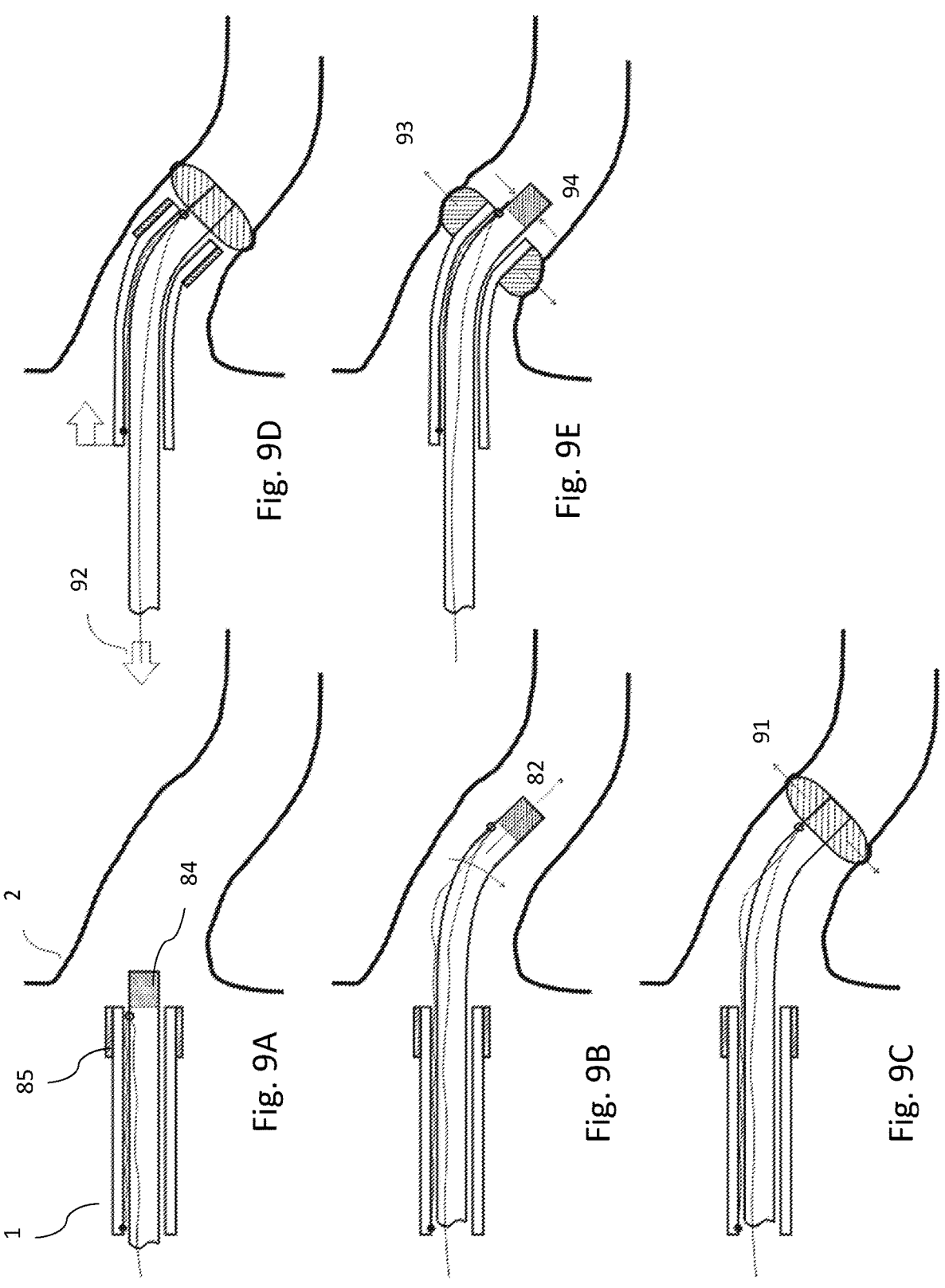
FIGS. 9A to 9E schematically illustrate the operation of an example endoscope according to the present invention

Referring to FIG. 8, there is shown the distal end of an endoscope 1 according to the invention. The endoscope 1 in FIG. 8 comprises an inner scope 82 with an inflatable balloon 84 and an outer sheath 83, which also has inflatable balloon 85. A pull-wire or cable 88 is secured to the outer sheath 83 at the proximal end of the endoscope 1 via an anchor point 87 and the cable 88 is threaded through a loop 86 at the distal end of the inner scope 82. Though the full length of the outer sheath 83 is not shown in FIG. 8, it is significantly longer than the cavity in which it is to be inserted in use.

The operation of the endoscope 1 according to the invention will now be described with reference to FIGS. 9A to 9E. The sequence of operation is to advance and steer the inner scope 82 within the cavity 2 as far as possible without impacting on the walls of the cavity 2. The balloon 84 is inflated 91 to anchor the inner scope 82 in position within the cavity 2. The cable 88 is then tensioned 92 and used to pull the outer sheath 83 up to the location of the tip of the inner scope 82. The balloon 85 on the outer sheath 83 is then inflated 93 to anchor the position of the outer sheath 83 and the balloon 84 on the inner scope 82 is deflated 94. This cycle of movement can be repeated in order to advance the endoscope 1 through the cavity 2.

The outer balloon 85 enables the operator to adjust the position of the inner scope 82 relative to the width of the cavity 2. This can increase the free travel available to the inner scope 82 so that it can advance further before impinging on the walls of the cavity 2.

The above sequence can be simplified by eliminating the outer balloon 85 and controlling the depth of the outer sheath 83 from outside of the cavity 2 either manually or via robotic control.

An alternative sequence of use is to advance the inner sheath 82 as before and then anchor via the inner balloon 84 in the advanced position. Then, rather than pulling on a cable 88 the outer sheath 83 is pushed relative to the inner scope 82 only.

Though the examples in FIGS. 7-9 use balloons as the anchor, other types of anchors could also be used such as the sleeve or the stabilising anchor comprising a resilient portion.

With the present invention it is possible to improve the insertion process of an endoscope within a patient to reduce the risk of injury to the patient and to ensure that the endoscope is deployed accurately.

Active Image Stabilisation

Active image stabilisation for an endoscope as described in FIG. 1 may be performed by obtaining images from one or more camera(s) 14, processing the images to determine motion, and controlling the endoscope to compensate for the motion.

Figure 10A:
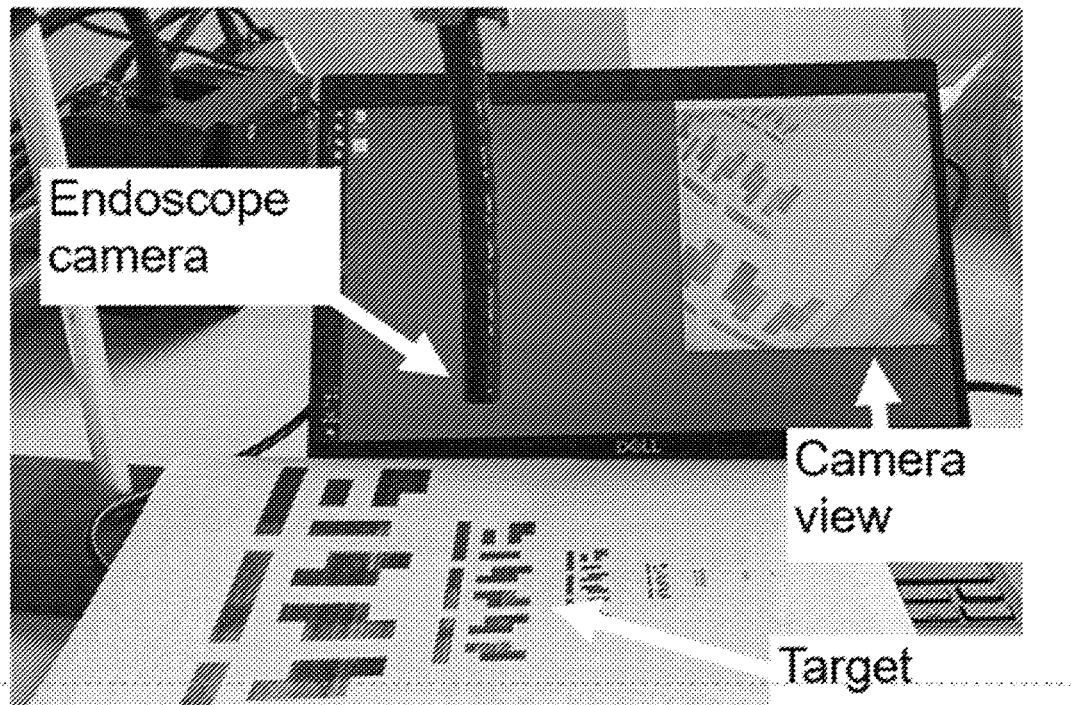
FIGS. 10A and 10B are schematic illustrations of an endoscope controlled according to a method as described herein.
Figure 10B:
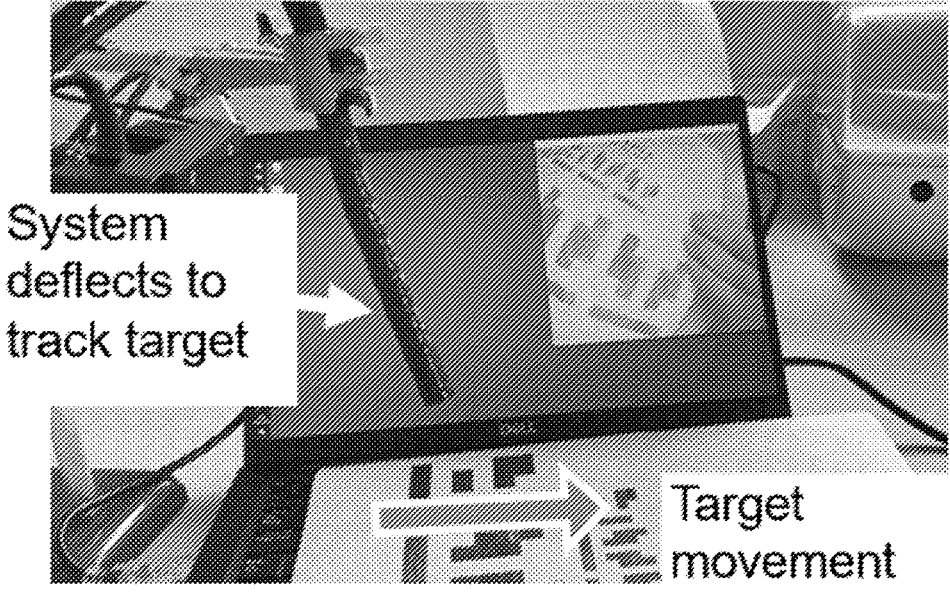

FIGS. 10A and 10B are schematic illustrations of an endoscope controlled according to such a method.

As shown in FIG. 10A, an endoscope is initially arranged with its camera 14 facing a sheet of paper comprising text. FIG. 10A also shows the camera's viewpoint on a computer screen.

As shown in FIG. 10B, when the paper moves and the associated text moves, the endoscope is deflected to compensate for the relative motion of the text visible in the camera's image. As shown on the computer screen, this means that the position of the text in the image remains similar to the position of the text in the image obtained in FIG. 10A.

Figure 11:
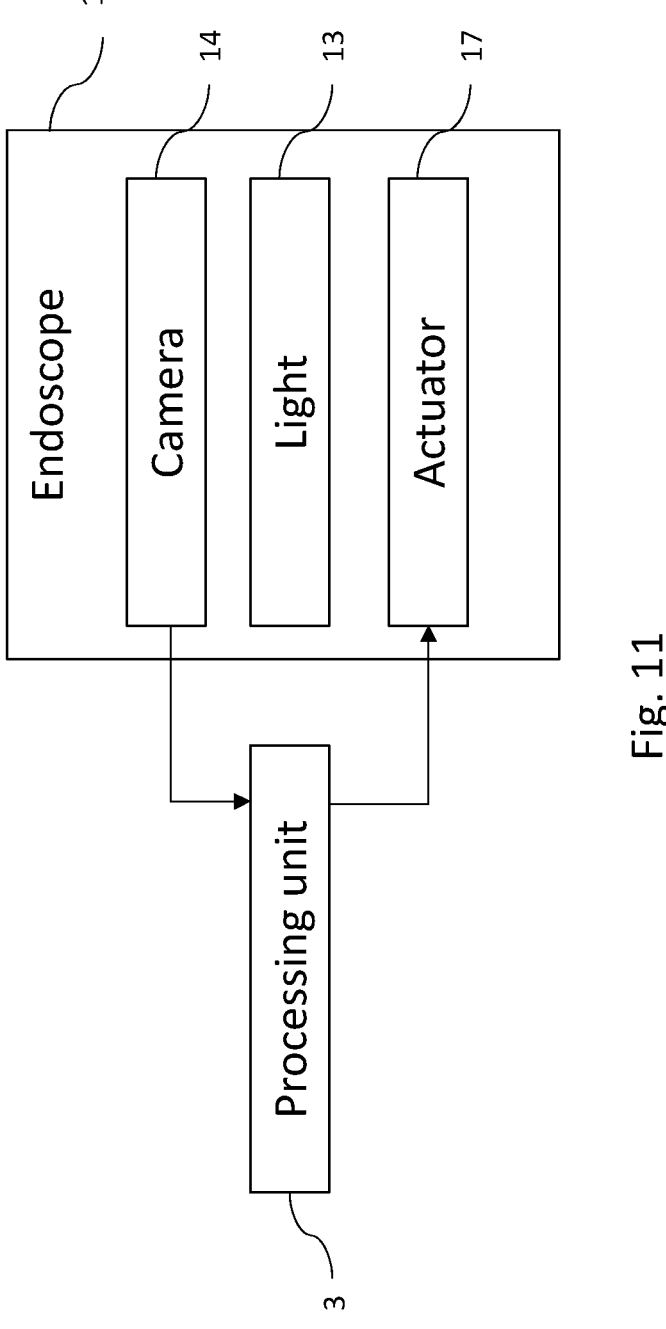
FIG. 11 is a schematic illustration of an endoscope system according to an embodiment.

FIG. 11 illustrates an endoscope system configured to control an endoscope according to such a method.

At least one camera 14 of the endoscope is communicatively connected to a processing unit 3. The processing unit 3 may be integrated with the endoscope 1, or may be a separate device to which the endoscope 1 is connected in use.

The endoscope is inserted into a patient to travel to, and observe or interact with a target area of an internal cavity of the patient. While the endoscope is travelling, or when the endoscope has reached the target area, the processing unit 3 is configured to obtain a series of images of the internal cavity from the viewpoint of the at least one camera 14, in order to perform motion compensation and stabilise the images obtained by the camera 14.

The processing unit 3 is further configured to compare a first and second image of the internal cavity obtained at different times by the camera 14 in order to determine an endoscope motion of the distal end portion of the endoscope that holds the camera 14, the endoscope motion being measured relative to a feature of the internal cavity.

More specifically, the processing unit 3 is configured to use a technique to identify aspects of the first image that appear in the second image, and calculate how much those aspects have moved between the two images.

Figure 12A:
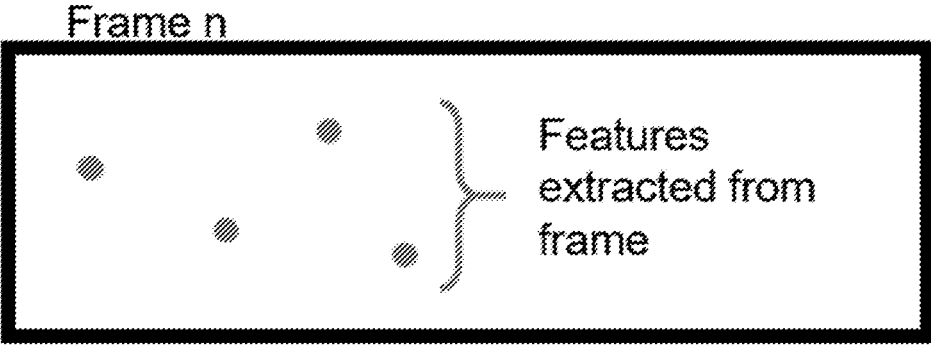
FIGS. 12A to 12C are schematic illustrations of processing for motion compensation based on feature tracking according to a method described herein.
Figure 12B:
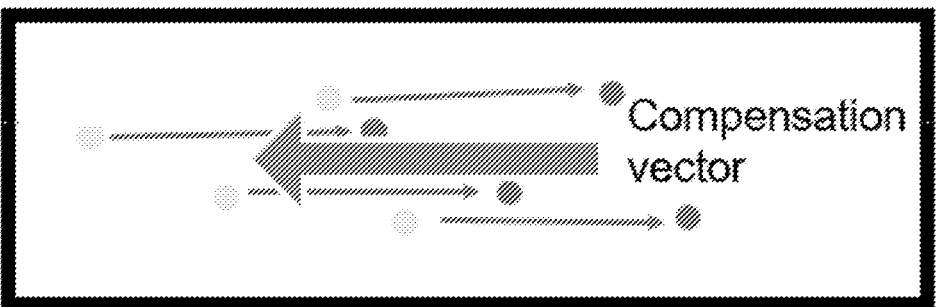
Figure 12C:
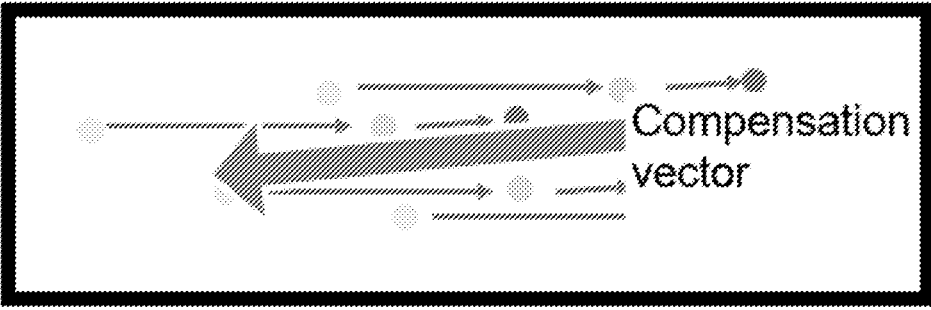

A first technique for identifying aspects and calculating motion is illustrated in FIGS. 12A to 12C.

Namely, as illustrated in FIG. 12A, in the first technique the processing unit 3 performs feature extraction to identifying a plurality of features and a position of each of the plurality of features in each image obtained from the camera 14. Feature extraction encompasses a variety of algorithms including general edge detection as well as techniques configured specifically for identifying features that are likely to occur in images of the interior of a body cavity.

Once a set of features has been identified in a first image and a second image, the motion of each feature can be calculated as the difference in position of the feature between the first image and the second image.

The individual motions of the features are then combined to give an estimate of the endoscope motion. In the simple case that it can be assumed the motion does not contain any rotation or 3D depth, then the endoscope motion can simply be the average of the individual motions of the features. On the other hand, more complex techniques preferably identify how far a feature is from the camera, and take into account the fact that apparent motion would be lower for features which are further from the camera 14, and take into account any rotation motion.

The first technique can be performed for any number of one or more features. In the case of only one feature, there is no need to combine individual motions of the features, but distance from the camera 14 can still be taken into account.

As illustrated in FIGS. 12B and 12C, this technique can be repeated over a series of motions, and a motion compensation vector can be applied based on successive pairs of images obtained from the camera 14. Here, the motion compensation vector may be an absolute displacement provided by bending the endoscope, or may be a force feedback applied as torque in the bending control of the endoscope.

Optionally, by recording a time at which each imager is obtained, the processing unit 3 can also determine a velocity of the endoscope, although this is not necessary for absolute compensation of motion.

Figure 13:
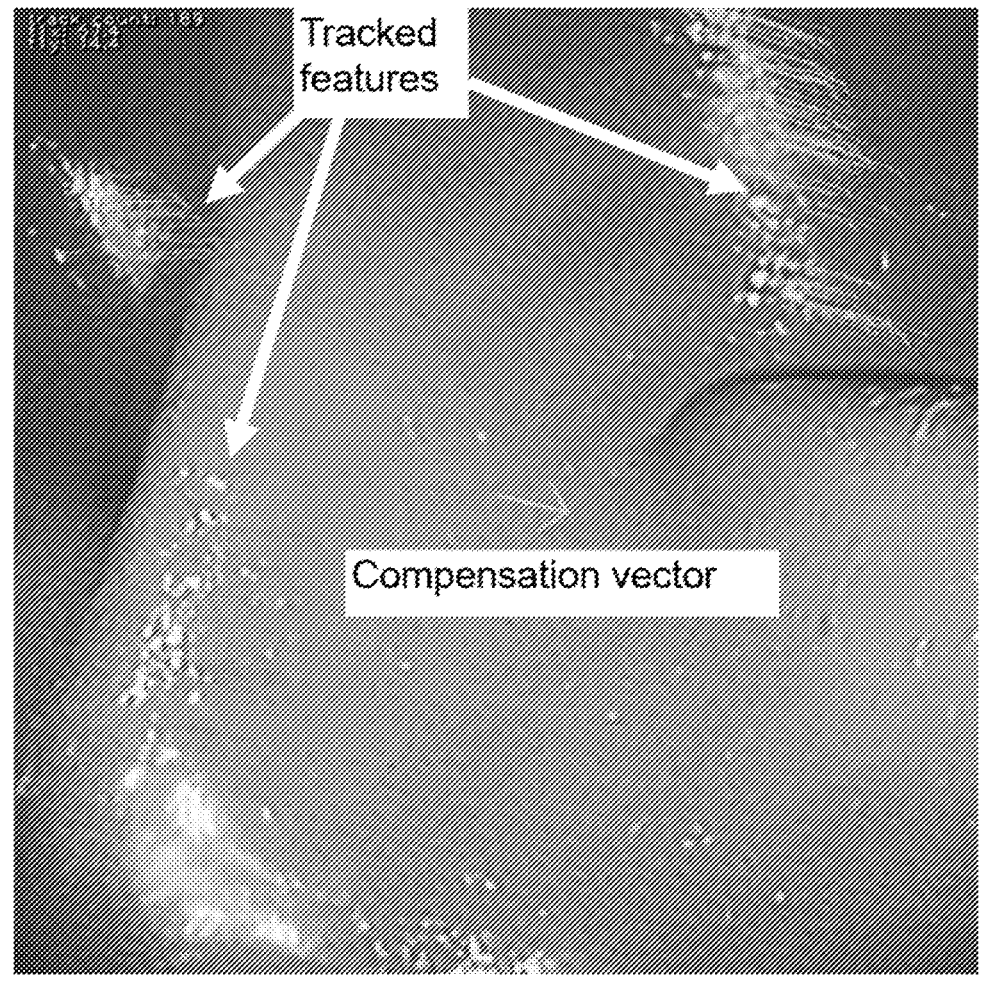
FIG. 13 is a schematic illustration of processing for motion compensation based on optical flow.

A second technique for identifying aspects and calculating motion is illustrated in FIG. 13.

In the second technique, features need not be explicitly identified, and optical flow can be calculated based on the first and second images as a whole. For example, as illustrated in FIG. 13, images may contain bright spots where the wall of the internal cavity is more reflective. By using optical flow analysis, the processing unit 3 can identify a displacement based on unguided processing of pixel values, without requiring the capability to identify features. This displacement is determined to be the endoscope motion.

Optical flow can preferably be calculated using the Lucas-Kanade method, which is effective at tracking irregular solid surfaces because it assumes regional uniformity of motion, and is therefore effective in tracking motion in a medical context.

Whichever way the endoscope motion is determined, the processing unit 3 is then configured to control an actuator to compensate for the endoscope motion.

In particular, a compensation vector can be determined as the opposite of the endoscope motion.

Once the compensation vector has been determined, one or more actuators 17 configured to control the bending of the endoscope are controlled to move a distal end of the endoscope (where the camera is hosted) so that the distal end moves by the compensation vector, and the imaging viewpoint of the camera remains stable while obtaining a series of images, and it becomes easier for an operator to understand what is being seen by the camera 14 of the endoscope. Additionally, by maintaining stability of this viewpoint, an operator is provided with a stable reference point for controlling any tools hosted by the distal end of the endoscope.

The actuator(s) 17 may be located in a proximal end of the endoscope 1 and may be connected to the above-described lines for operating vertebra of the tubular body 16. Alternatively, the actuator(s) may be located within the tubular body 16 and may be electronically controlled to drive mechanical motion from as close as possible to the vertebra which participate in the bending.

As mentioned above, image stabilisation may be performed when the endoscope is travelling to, and observing or interacting with a target area of an internal cavity of the patient.

In the case of observing or interacting with the target area, the image stabilisation may ensure that the distal end of the endoscope continues to face the target area. On the other hand, when the endoscope is travelling, the features visible to the endoscope are expected to change. In order to maintain image stabilisation and assist an operator in guiding the endoscope towards its target area, the processing unit 3 may stabilise the image to face a random part of a wall of the internal cavity of the patient for as long as possible, before selecting a new random part of the wall. This means that, from the operator's perspective, the endoscope views a relatively stable part of the internal cavity, and travels directly towards the selected stable part of the internal cavity. As a result, the direction in which the camera 14 of the endoscope is targeted changes less frequently, and the images obtained by the camera 14 are easier for an operator to interpret in order to properly guide the endoscope.

Figure 14:
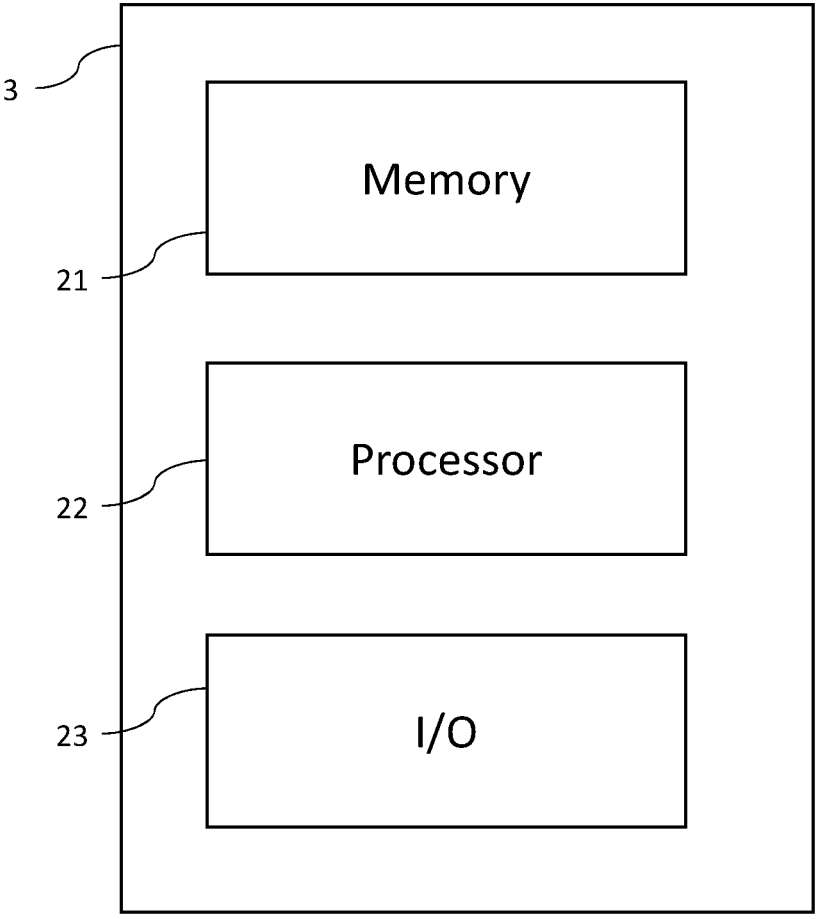
FIG. 14 is a schematic illustration of a processing unit of the embodiment.

FIG. 14 is a schematic illustration of a processing unit of the embodiment.

The processing unit 3 may comprise standard computing hardware, including a memory 21 storing instructions for performing a method according to the invention, a processor 22 for executing the method to control the endoscope 1, and an input/output interface 23 for receiving image data from the camera 14 and transmitting control data to the actuator 17. The method for processing images and controlling the actuator may be hard-coded in custom hardware, such as an application specific integrated chip (ASIC). Additionally, processing instructions defining the method may be stored in a portable form such as a digital signal or instruction data stored in a computer-readable storage medium such as a flash memory or CD.

Figure 15A:
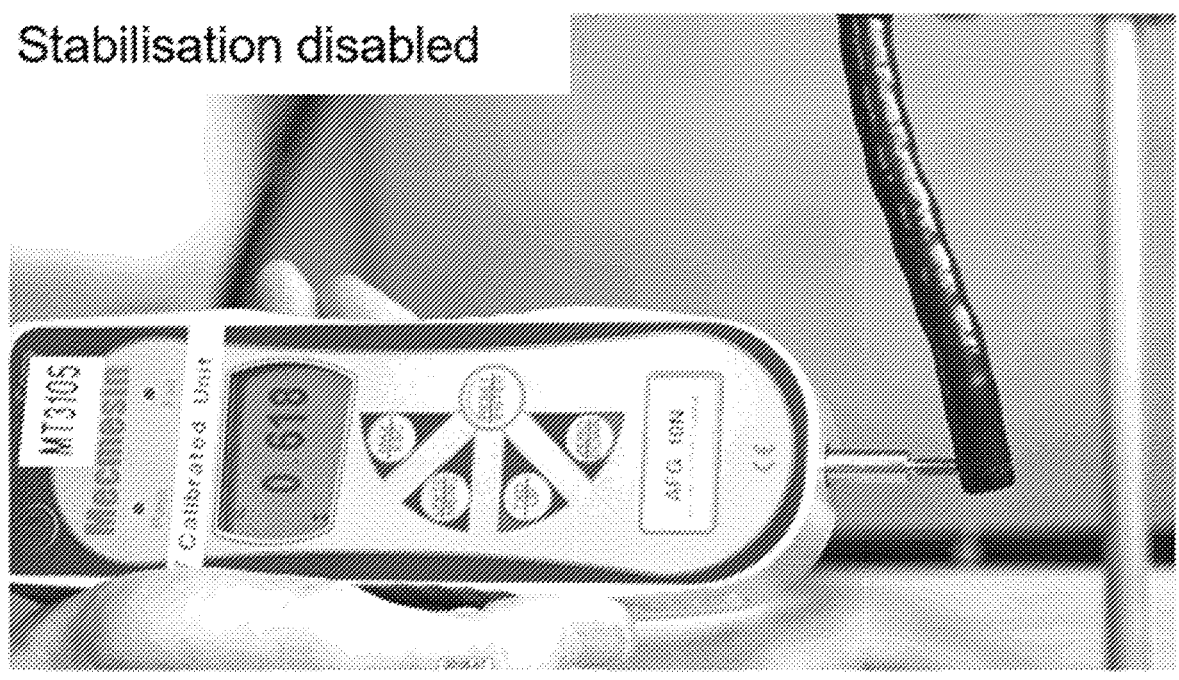
FIGS. 15A and 15B are schematic illustrations of an endoscope controlled with force feedback.
Figure 15B:
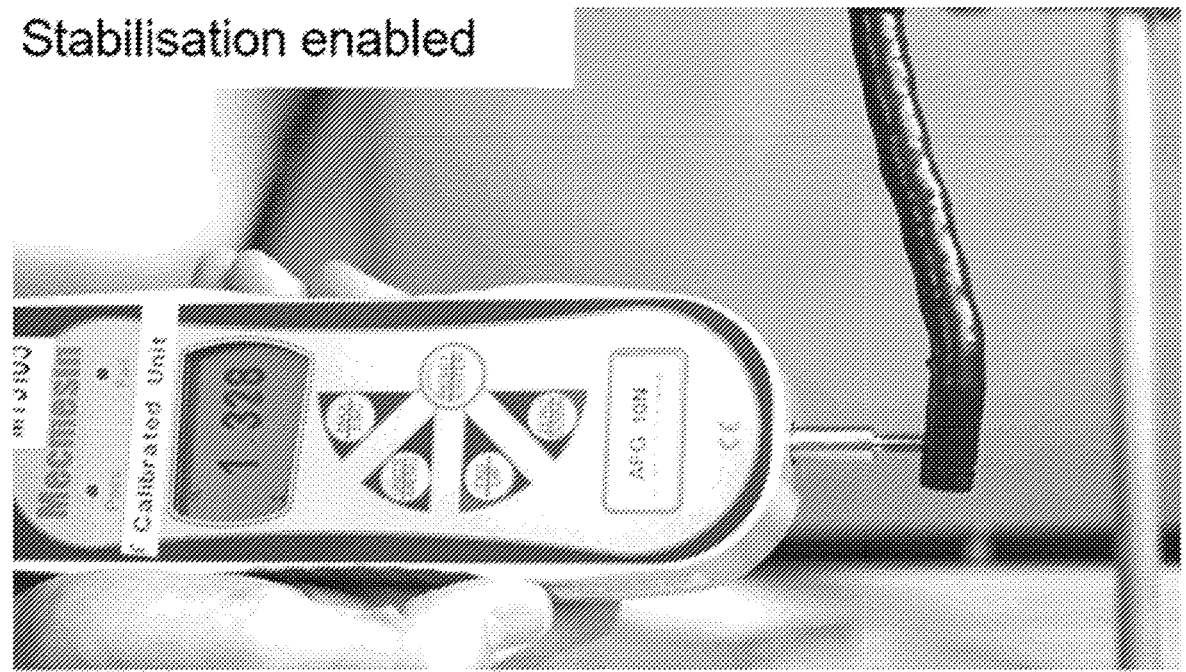

FIGS. 15A and 15B are schematic illustrations of an endoscope controlled with force feedback.

As illustrated in FIGS. 15A and 15B, the endoscope system may be configured to control the one or more actuators 17 to apply not just a fixed displacement based on a determined endoscope motion, but also a continuous force to maintain the endoscope in a stable position.

More specifically, in FIGS. 15A and 15B, a photograph is shown of a test scenario where an endoscope is pushed using a force meter, and a reaction force from the endoscope applied to the force meter is displaced on the screen of the force meter.

In FIG. 15A, no stabilisation is enabled, and it can be seen that the endoscope both faces a different direction and applies less of a reaction force to try to maintain its original position, when compared to the situation shown in FIG. 15B.

In FIG. 15B, the processing unit 3 has controlled the actuators 17 in the distal end of the endoscope so that the endoscope bends in order to face towards its original direction. This bending comes in the form of a continuous applied force, as measured by the force meter.

Figure 16:
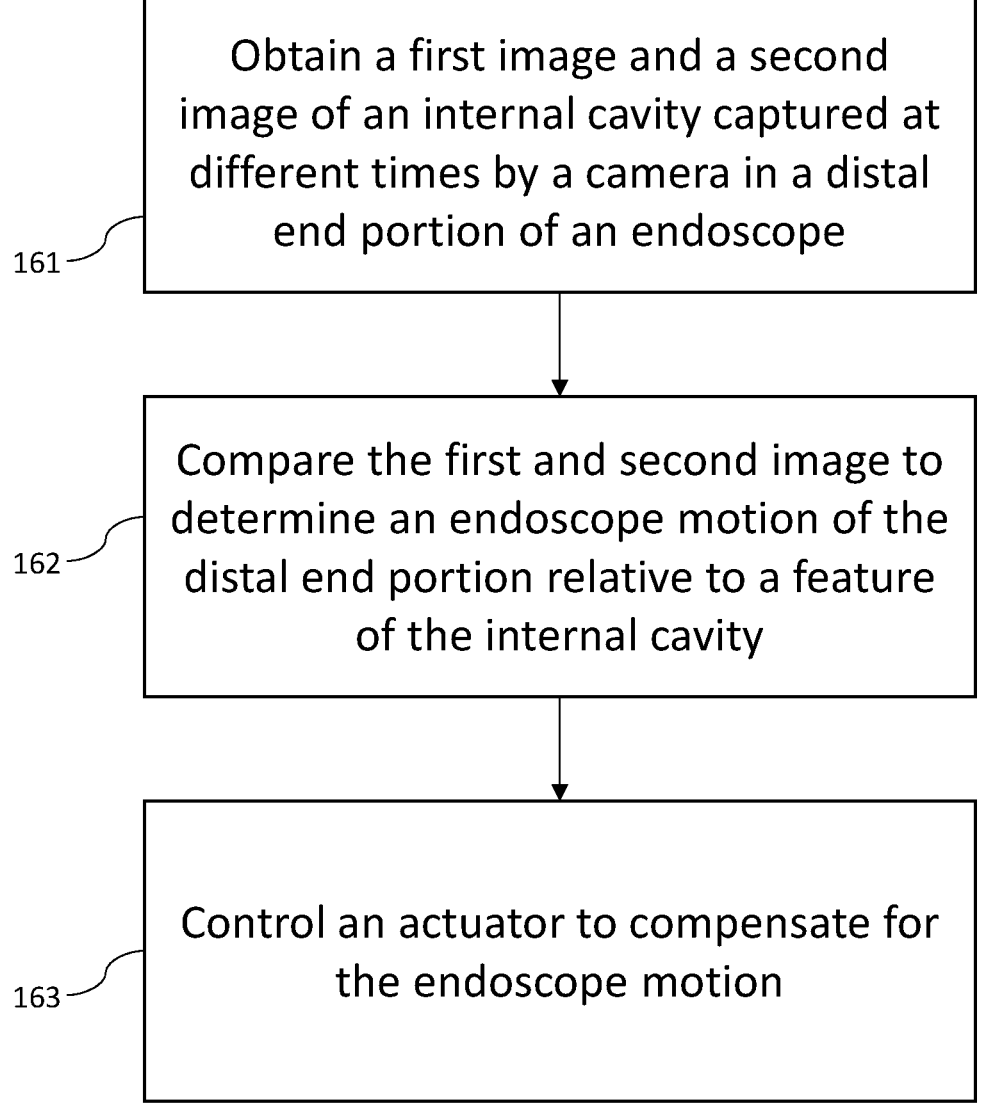
FIG. 16 is a flow chart schematically illustrating a method of image stabilization.
Figure 17:
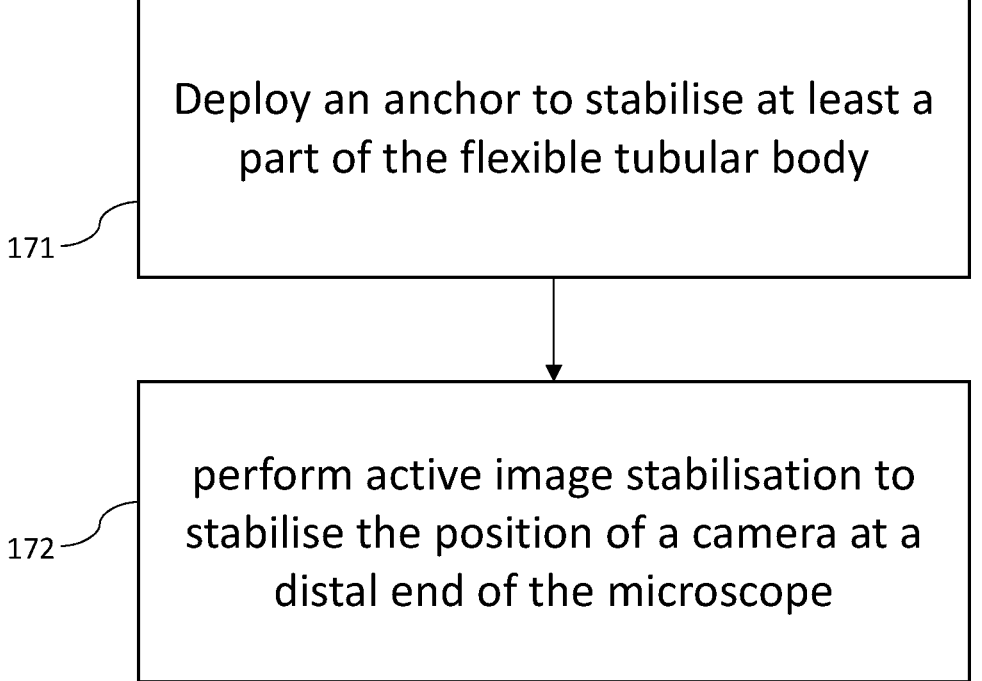
FIG. 17 is a flow chart schematically illustrating a method of image stabilization.

FIG. 16 is a flow chart schematically illustrating a method performed by the processing unit 3. This is a method which may be used for operating an endoscope with increased stability of the distal end of the endoscope. The method is preferably automated using a processor configured to receive image data from the endoscope camera 14 and to control an actuator 17 for controlling a stability of the endoscope.

In step 161, the processor obtains a first image and a second image of an internal cavity captured at different times by the camera 14 in a distal end portion of the endoscope 1. This can be achieved by providing a data connection between the camera 14 and the processor. The connection could in some cases be a wireless connection or a connection via the World Wide Web where the endoscope operator is remote from the patient.

In step 162, the processor compares the first and second image obtained from the camera 14 to determine an endoscope motion of the distal end portion of the endoscope relative to a feature of the internal cavity. This step may for example be performed using the techniques illustrated in FIGS. 4A to 5, and as described above in relation to the corresponding features of the endoscope system.

In step 163, the processor controls the actuator to compensate for the endoscope motion. This may be performed using a data connection between the processor and the actuator 16, which may be a wireless connection or a connection via the World Wide Web in a case where the endoscope operator is remote from the patient.

Active Anchor Control

Further to the above-described anchors and active image stabilization techniques, image stabilization may be further enhanced by performing active control of an anchor based on images processed for image stabilization.

In particular, adjusting or relocating an anchor can have a large effect on stability of the distal end of an endoscope. This can be used in combination with more direct control of the shape of the endoscope to provide image stabilization with fine tuning over a wide range of circumstances. Thus anchors and image stabilization can be used synergistically together to provide a greater stabilisation than the sum of their individual contributions.

To explain this in more detail, stability is significantly dependent on a length of the endoscope that is free floating within the body cavity that is reached by the endoscope. The tubular body of the endoscope has some flexibility, and the longer the free standing part of the tubular body, the lower its stiffness, and thus the more it moves when jolted. By anchoring at least part of the tubular body, this free length can be shortened and/or controlled, and it is only necessary to provide active stabilisation for the remaining free standing part between the anchor and the distal end of the endoscope.

As explained above with reference to FIG. 6, in some embodiments the anchor 12 is attached via a slider 122, and thus the free length of the tubular body can be varied while the anchor is in place and expanded. Thus, when the endoscope is sufficiently stable, a free length can be increased to allow a greater range of motion for the endoscope operator, and when the endoscope is not sufficiently stable, the free length can be decreased.

The processing unit 3 may be configured to automatically evaluate image stability using a moving image stability metric. For example, the processing unit 3 may record a moving root mean square (RMS) average and/or variance of endoscope motion between pairs of obtained images. This moving image stability metric may be compared to one or more predetermined thresholds to give a categorised analysis of image stability.

Once image stability has been categorised, the processing unit 3 may automatically use measures to improve image stability if it is too low, or to increase operator freedom if image stability is higher than it needs to be.

For example, if image stability is below a predetermined lower threshold, the processing unit 3 may automatically control the endoscope 1 to perform any of: redeploying a deployed anchor to reduce a distance between the anchor and a distal end of the flexible tubular body; deploying an additional anchor between an already-deployed anchor and a distal end of the flexible tubular body; and controlling a deployed anchor to increase an anchoring strength. With respect to the first of these, changing the distance between the anchor and a distal end of the flexible tubular body may be performed using a slider 122 if a slider is included in the particular embodiment of the anchor 12. With respect to the last of these, an anchoring strength may be increased by increasing a size or stiffness of an expandable anchor. If the anchor is an inflatable anchor, additional fluid may be pumped into the anchor to increase size or stiffness.

Similarly, if image stability is above a predetermined upper threshold, the processing unit 3 may automatically control the endoscope 1 to perform any of: redeploying a deployed anchor to increase a distance between the anchor and a distal end of the flexible tubular body; removing a deployed anchor; and controlling a deployed anchor to decrease an anchoring strength. With respect to the first of these, changing the distance between the anchor and a distal end of the flexible tubular body may be performed using a slider 122 if a slider is included in the particular embodiment of the anchor 12. With respect to the last of these, an anchoring strength may be decreased by decreasing a size or stiffness of an expandable anchor. If the anchor is an inflatable anchor, fluid may be released from the anchor to decrease size or stiffness.

Image stabilisation can also be improved using the off-centre anchoring described above with reference to FIG. 3. More specifically, by anchoring the endoscope off-centre using a plurality of anchors which expand to different widths, the distal end of the endoscope can be aimed at a target feature on the wall of the cavity or lumen, rather than being directed further along the cavity or lumen. This means that the tendon-type control of vertebrae requires a less extensive bend to direct the distal end of the endoscope towards the target feature, and a greater range of the line-controlled motion remains available for compensating motion and improving stabilisation.

The invention claimed is:

1. An endoscope system for remotely observing a target area of an internal cavity of a patient, the endoscope system comprising:
   an endoscope comprising:
      a flexible tubular body with a distal end portion that reaches the internal cavity in use,
         wherein the distal end portion includes:
            at least one camera configured to capture images of the internal cavity,
            at least one light to illuminate the internal cavity for imaging, and
            at least one working channel to extend tools into the internal cavity,
      at least one anchor arranged circumferentially around the flexible tubular body to stabilize the distal end portion within the internal cavity; and
   a processing unit comprising a memory and at least one processor configured to:
      capture a first image of the internal cavity at a first time,
      capture a second image of the internal cavity at a second time,
      calculate a displacement of the distal end portion by comparing the first image and the second image;
      perform active image stabilization to stabilize a position of the at least one camera at the distal end portion of the flexible tubular body; and
      calculate image stability and, when the image stability is below a predetermined lower threshold, control a position, a size, an anchoring strength, or a quantity of the at least one anchor to reduce motion of the distal end portion of the flexible tubular body.

2. The endoscope system of claim 1, wherein performing active image stabilisation comprises controlling a bending shape or a bending force in a portion of the flexible tubular body between the at least one anchor and the distal end portion of the flexible tubular body.

3. The endoscope system of claim 2, wherein the bending shape or the bending force is controlled such that force feedback is applied to the flexible tubular body to control a position of the distal end portion.

4. The endoscope system of claim 1, wherein calculating the displacement comprises:
   identifying a plurality of features and corresponding positions of each of the plurality of features in the first image;
   locating, in the second image, the plurality of features identified in the first image;

calculating the displacement of each of the plurality of features by comparing feature positions in the first image with positions of corresponding features in the second image; and calculating a motion compensation vector based on an average of the displacement of the plurality of features.

5. The endoscope system of claim 1, wherein calculating the displacement comprises calculating optical flow between the first image and the second image.

6. The endoscope system of claim 5, wherein the optical flow between the first image and the second image is calculated using a Lucas-Kanade algorithm.

7. The endoscope system of claim 1, wherein the at least one anchor is attached to the flexible tubular body via a slider defining a range of movement of the flexible tubular body relative to the at least one anchor, and wherein performing active image stabilisation comprises controlling a position of the flexible tubular body relative to the at least one anchor.

8. The endoscope system of claim 7, wherein the slider is configured to move axially along the flexible tubular body.

9. The endoscope system of claim 1, wherein the at least one processor is further configured to, and when the image stability is above a predetermined upper threshold, remove an anchor or reducing the anchoring strength of the at least one anchor.

10. The endoscope system of claim 9, wherein the at least one anchor is an expandable anchor and wherein increasing the anchoring strength comprises increasing the size or a stiffness of the at least one anchor and reducing the anchoring strength comprises reducing the size or the stiffness of the at least one anchor.

11. The endoscope system of claim 10, wherein the at least one anchor is an inflatable balloon which is activated by inflation and configured to expand between the distal end portion of the flexible tubular body and a wall of the internal cavity.

12. The endoscope system of claim 1, wherein the at least one anchor comprises a plurality of expandable anchors located circumferentially around the flexible tubular body, wherein a first expandable anchor of the plurality of expandable anchors is configured to expand to a greater width than a second anchor of the plurality of expandable anchors.

13. The endoscope system of claim 1, wherein the flexible tubular body further comprise a proximal end portion configured to remain outside the patient and a fluid connection between the proximal end portion and the at least one anchor of the distal end portion.

14. A method of stabilizing images captured by an endoscope of a target area of an internal cavity of a patient, the method comprising:

illuminating at least one light, wherein the at least one light is provided at a distal end portion of flexible tubular body of the endoscope;

capturing, by at least one camera, a first image of the internal cavity at a first time, wherein the at least one camera is provided at the distal end portion of the flexible tubular body of the endoscope;

capturing, by the at least one camera, a second image of the internal cavity at a second time;

calculating a displacement of the endoscope by comparing the first image to the second image;

performing, by at least one anchor, active image stabilization to stabilize a position of a distal end of the endoscope, wherein the at least one anchor is arranged circumferentially around the flexible tubular body of the endoscope; and calculating image stability and, when the image stability is below a predetermined lower threshold, controlling a position, a size, an anchoring strength, or a quantity of the at least one anchor to reduce motion of the distal end portion of the flexible tubular body.

15. The method of claim 14, wherein calculating the displacement comprises:

identifying a plurality of features and corresponding positions of each of the plurality of features in the first image;

locating, in the second image, the plurality of features identified in the first image;

calculating the displacement of each of the plurality of features by comparing positions of each of the plurality of features in the first image with new positions of each of the plurality of features in the second image; and calculating a motion compensation vector based on an average of the displacement of the plurality of features.

16. The method of claim 14, wherein calculating the displacement comprises calculating optical flow between the first image and the second image.

17. The method of claim 16, wherein the optical flow between the first image and the second image is calculated using a Lucas-Kanade algorithm.

18. The method of claim 14, further comprising, when the image stability is above a predetermined upper threshold, removing an anchor or reducing the anchoring strength of the at least one anchor.

19. The method of claim 14, further comprising controlling a bending shape or a bending force in a portion of the flexible tubular body between the at least one anchor and the distal end portion of the flexible tubular body.

20. The method of claim 14, wherein the at least one anchor is attached to the flexible tubular body via a slider defining a range of movement of the flexible tubular body relative to the at least one anchor, and wherein performing active image stabilisation comprises controlling a position of the flexible tubular body relative to the at least one anchor.

* * * * *